United States Patent
Barbour et al.

(10) Patent No.: US 11,037,677 B2
(45) Date of Patent: Jun. 15, 2021

(54) FAST, CONTINUOUS PSYCHOMETRIC ESTIMATION SYSTEM UTILIZING MACHINE LEARNING AND ASSOCIATED METHOD OF USE

(71) Applicants: Dennis Barbour, Saint Louis, MO (US); Xinyu Song, Saint Louis, MO (US); Noah Ledbetter, Saint Louis, MO (US); Jacob Gardner, Saint Louis, MO (US); Kilian Weinberger, Saint Louis, MO (US)

(72) Inventors: Dennis Barbour, Saint Louis, MO (US); Xinyu Song, Saint Louis, MO (US); Noah Ledbetter, Saint Louis, MO (US); Jacob Gardner, Saint Louis, MO (US); Kilian Weinberger, Saint Louis, MO (US)

(73) Assignee: WASHINGTON UNIVERISTY, St. Louis, MO (US)

( * ) Notice: Subject to any disclaimer, the term of this patent is extended or adjusted under 35 U.S.C. 154(b) by 416 days.

(21) Appl. No.: 15/551,463

(22) PCT Filed: Feb. 19, 2016

(86) PCT No.: PCT/US2016/018595
§ 371 (c)(1),
(2) Date: Aug. 16, 2017

(87) PCT Pub. No.: WO2016/134212
PCT Pub. Date: Aug. 25, 2016

(65) Prior Publication Data
US 2018/0042541 A1    Feb. 15, 2018

Related U.S. Application Data

(60) Provisional application No. 62/118,262, filed on Feb. 19, 2015.

(51) Int. Cl.
*A61B 5/16* (2006.01)
*A61B 5/12* (2006.01)
(Continued)

(52) U.S. Cl.
CPC ............. *G16H 40/63* (2018.01); *A61B 5/125* (2013.01); *A61B 5/163* (2017.08); *A61B 5/24* (2021.01); *A61B 5/25* (2021.01); *G16H 50/20* (2018.01)

(58) Field of Classification Search
None
See application file for complete search history.

(56) References Cited

U.S. PATENT DOCUMENTS

| | | |
|---|---|---|
| 2005/0175972 A1 | 8/2005 | Goldman et al. |
| 2008/0091118 A1 | 4/2008 | Georgopoulos |

(Continued)

OTHER PUBLICATIONS

Kontsevich, et al., "Bayesian adaptive estimation of psychometric slope and threshold", Vision Research, 1999, pp. 2729-2737, vol. 39.

(Continued)

*Primary Examiner* — Eric F Winakur
*Assistant Examiner* — Marjan Fardanesh
(74) *Attorney, Agent, or Firm* — Thompson Coburn LLP (57) ABSTRACT

A method and system for of computerized psychometric testing of sensory information that includes selecting stimulus parameters for a first stimulus to be applied with a stimulus inducer, applying a first stimulus on a subject with the stimulus inducer upon command of a processor, calculating a posterior probability function and an acquisition function at least based on the subject's response to the first stimulus with the processor, determining stimulus parameters for a second stimulus based on the calculated acquisition function with the processor, stimulating the subject with the second stimulus with the stimulus inducer upon (Continued)

command of the processor, and determining a detection threshold function by calculating the posterior probability function at least based on the subject's response to the second stimulus with the processor.

19 Claims, 5 Drawing Sheets

(51) Int. Cl.
*G16H 40/63* (2018.01)
*G16H 50/20* (2018.01)
*A61B 5/24* (2021.01)
*A61B 5/25* (2021.01)

(56) References Cited

U.S. PATENT DOCUMENTS

| | | |
|---|---|---|
| 2008/0208072 A1 | 8/2008 | Fadem et al. |
| 2009/0286211 A1 | 11/2009 | Eisenhardt et al. |
| 2010/0007851 A1 | 1/2010 | Lu et al. |
| 2010/0068684 A1 | 3/2010 | Sabel |
| 2011/0077546 A1 | 3/2011 | Fabian |
| 2012/0197153 A1* | 8/2012 | Kraus ............... A61B 5/04845 600/545 |

OTHER PUBLICATIONS

International Search Report and Written Opinion for International Patent Application PCT/US2016/018595 dated May 6, 2016, 12 pages.
International Preliminary Report on Patentability (Chapter1) for PCT/US2016/018595 dated Aug. 31, 2017.

\* cited by examiner

FAST, CONTINUOUS PSYCHOMETRIC ESTIMATION SYSTEM UTILIZING MACHINE LEARNING AND ASSOCIATED METHOD OF USE

RELATED APPLICATION DATA

The present application is a U.S. National Phase Application of PCT/US2016/018595, filed on Feb. 19, 2016, which claims the benefit of U.S. Provisional Patent Application Ser. No. 62/118,262, filed on Feb. 19, 2015, the disclosures of which are both incorporated by reference herein in their entireties.

BACKGROUND

Sensory organs consist of arrays of individual sensory elements such as photoreceptors in the retina, hair cells in the auditory and balance organs, and touch/pain receptors in the skin. The health of these sensory elements reflects disease states and is useful to know for diagnostic purposes.

One division of the field of psychometrics is concerned with determining a sensory organ's sensitivity. Psychometrics has developed testing methods to determine estimates of a sensory organ's detection threshold by querying subjects, and the testing procedure depends upon which sensory organ a psychometrician is testing. Detection thresholds are an indicator of sensory organ health, and can be useful in diagnosing sensory failure. For example, a detection threshold found from applying an audiogram test to a subject is used to diagnose hearing loss and to program a hearing aid for a person with hearing loss.

While some changes have occurred in psychometric testing methods over the years, most psychometric tests conducted still follow the same general format. A conventional psychometrics test generally changes the intensity of a stimulus with all other variables held constant and determines whether the subject can detect the stimulus through feedback provided by the subject. By systematically altering the intensity of the stimulus above and below a detection threshold, the actual threshold value can be narrowed down for that location on the sensory organ. For example, a psychometrician may administer an audiogram test to a subject by varying a sound's intensity above and below the detection threshold for a given frequency until the detection threshold is found. Using the resulting data, an estimated detection threshold may be found for the subject at that frequency. The conventional audiogram method varies only the intensity of a tone at a single frequency until the detection threshold has been estimated within a tolerance level. That is, the conventional audiogram methods do not vary both the frequency and intensity of a stimulus from trial-to-trial. In other words, the conventional testing procedures only vary one variable at a time during testing.

Conventional audiograms typically employ the Hughson-Westlake procedure at six frequencies: 0.25, 0.5, 1, 2, 4, and 8 kHz. This adaptive procedure proceeds frequency-by-frequency with the presentation of a tone at various intensities, and after presentation of each tone, a psychometrician logs the subject's response. A subject's response is typically a hand raise indicating that the subject heard the tone. At each of these six frequencies, a first intensity sound is delivered at a level audible to the subject, then it is reduced in fixed-size increments until the subject no longer responds. The intensity is then increased by a smaller fixed-size increment until the subject again responds. This procedure is repeated for several "reversals."

Conventional psychometric testing procedures, such as the Hughson-Westlake procedure, are very time consuming for both the subject of the test and the expert administering the test. Typically, psychometric tests are conducted manually and require substantial labor on the part of the psychometrician, thereby representing a relatively poor use of the psychometrician's level of expertise. In addition, the conventional testing procedures estimate the detection threshold only at a few discrete locations (e.g., the frequencies 0.25, 0.5, 1, 2, 4, and 8 kHz).

Various automated audiogram testing methods have been attempted over the years such as by giving listeners control of an attenuator rather than having subjects simply raise their hand to indicate whether they heard the sound or not. However these automated procedures still only estimate the detection threshold at the standard audiogram frequencies and are still time-consuming for the subject. Millions of these tests are administered to subjects every year, so even a slight improvement in efficiency could represent significant cost savings to administer these audiograms and other psychometric tests.

While the Hughson-Westlake method discussed above is directed to an audio detection threshold, psychometric tests directed at other sensory organs suffer the same deficiencies. Thus, there is a need for efficient and accurate psychometric testing methods.

SUMMARY

It is in view of the above problems that the present invention was developed. The invention is a machine learning psychometric estimation procedure that finds detection thresholds as a continuous function of all variables. For example, for hearing testing, the machine learning audiogram estimation procedure is able to estimate hearing thresholds continuously across all frequencies audible to the human ear. The procedure disclosed herein evaluates a sensory organ using a Gaussian process algorithm to construct audiogram estimates in real time. The Gaussian process is a machine-learning technique that allows for rapid and accurate estimation of multi-dimensional surfaces by constructing a Bayesian estimate of a function based upon a prior distribution of probabilities for that function. The Gaussian process is particularly well-suited for automated psychometric testing because 1) the Gaussian process's predictive posterior probability function can provide an estimate of the entire parameter space after each sample, and 2) the Gaussian process contains a built-in measure of confidence of the estimate in the shape of the distribution of the posterior probability function.

The system for psychometric testing stimulates a subject's sensory organ (skin, eyes, ears, etc.) and calculates an estimated detection threshold by applying the Gaussian process. Furthermore, the Gaussian process is trained to predict the probability of detection for any given stimulus as a function of any number of variables, which in the audiogram example are frequency and intensity. Once the confidence level rises above a threshold, the test completes and the system determines the detection threshold across all audible frequencies.

The system further leverages the Gaussian process posterior to identify points of informative testing with respect to some quality measure defined by an acquisition function. Using the posterior, the system is able to determine values of variables contributing to the highest acquisition function value. For example, testing the point having the highest variance value or highest mutual information value will inform the system of a more accurate estimation of the detection threshold. This process is called Bayesian active learning. After finding the testing point with the highest acquisition function value, the system stimulates the subject using the variable values corresponding to this point.

The informative sampling and the machine learning techniques described herein results in substantial increases in efficiency. The time necessary to test a subject may be two to ten times faster than conventional psychometric testing techniques, depending upon the nature of the psychometric task. Furthermore, the informative sampling methods means that stimuli are not presented only at standard variables (e.g. at standard frequencies for audiograms), but across all variables. More specifically for an audiogram, the more informative sampling method may select any frequency for testing rather than only one of the six standard frequencies. The result of informative sampling across all audible frequencies is a more accurate audiogram estimation at non-standard frequencies.

In one illustrative, but nonlimiting embodiment, a method of computerized psychometric testing of sensory information comprises selecting stimulus parameters for a first stimulus to be applied with a stimulus inducer, applying a first stimulus on a subject with the stimulus inducer upon command of a processor, calculating a posterior probability function and an acquisition function at least based on the subject's response to the first stimulus with the processor, determining stimulus parameters for a second stimulus based on the calculated acquisition function with the processor, stimulating the subject with the second stimulus with the stimulus inducer upon command of the processor, and determining a detection threshold function by calculating the posterior probability function at least based on the subject's response to the second stimulus with the processor.

In another illustrative, but nonlimiting embodiment, a computerized psychometric testing system of sensory information comprises a stimulus inducer configured to apply a stimulus to a subject, an input device configured to send data indicating whether the subject responded to the stimulus applied by the stimulus inducer, and a processor configured to select stimulus parameters for a first stimulus to be applied to a subject, command the stimulus inducer to stimulate the subject with the first stimulus, receive data from the input device indicating whether the subject responded to the first stimulus, calculate a posterior probability function and an acquisition function at least based on the subject's response to the first stimulus, determine stimulus parameters for a second stimulus based on the calculated acquisition function, command the stimulus inducer to stimulate the subject with the second stimulus, receive a signal from the input device indicating whether the subject responded to the second stimulus, and determine a detection threshold function by calculating the posterior probability function based on the subject's response to at least the second stimulus.

In yet another illustrative, but nonlimiting embodiment, a method for informative psychometric test sampling comprises calculating an acquisition function of the predictive posterior probability function such as variance or mutual information, determining the variable set contributing to the acquisition function value, and stimulating a subject with a stimulus having parameters corresponding to the variable set contributing to the highest acquisition function.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

DETAILED DESCRIPTION OF THE PREFERRED EMBODIMENT

Figure 1:
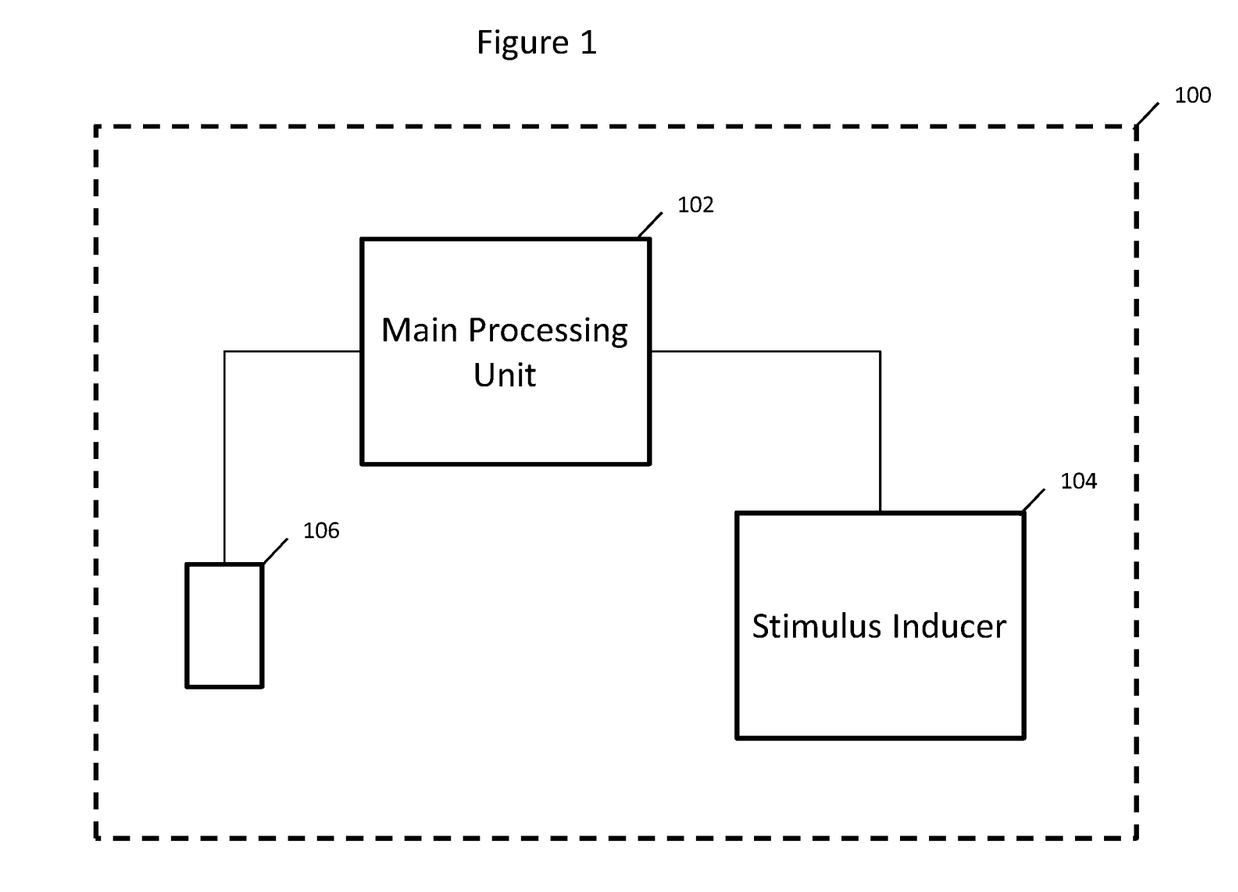
FIG. 1 illustrates a system used to administer the psychometric test according to an exemplary embodiment.

Referring to the accompanying drawings in which like reference numbers indicate like elements, FIG. 1 illustrates a system 100 used to administer the psychometric test. The system 100 includes a main processing unit 102, a stimulus inducer 104, and an input device 106.

The main processing unit 102 is specially configured to command the stimulus inducer 104 to variably stimulate a subject and receive signals from the input device 106. The main processing unit 102 is further configured to estimate the detection threshold using pre-configured algorithms. The pre-configured algorithms executed by the main processing unit 102 determine a detection threshold function, a covariance function, hyperparameters, a predictive posterior function, and an informative sampling point. The main processing unit 102 may store the responses of the subject based on data received from the input device 106.

The stimulus inducer 104 is configured to provide a stimulus to a subject at the direction of the main processing unit 102. The stimulus inducer 104 may vary depending on the psychometric test being performed. For example, the stimulus inducer 104 may be a pair of headphones for audio stimulation, a light field for visual stimulation, a visual display for visual stimulation, a refreshable braille display for somatosensory stimulation, a rotating chair for vestibular stimulation, or any other type of device configured to stimulate a subject. In response to a signal from the main processing unit 102, the stimulus inducer 104 stimulates the subject according to the direction of the main processing unit 102. The signal sent to the stimulus inducer 104 from the main processing unit 102 may include variable parameters that define the stimulus to be applied to the subject. These parameters may include sound intensity, sound frequency, somatosensory intensity, location where somatosensory stimulus is applied, light intensity, coordinates for a visual stimulus, acceleration at which a chair will rotate, chair rotation angle, or any other parameter defining a stimulus. For example, if the stimulus inducer 104 is a pair of headphones, the headphones will generate a sound at the frequency and intensity determined by the main processing unit 102.

The input device 106 sends signals to the main processing unit 102 indicating whether the subject responded to the stimulus applied by the stimulus inducer 104. Detecting reactions to the stimulus provided by the stimulus inducer 104 may be determined by a variety of methods or collected using a variety of devices. The input device 106 may be an on/off push button device whereby a button push indicates that the subject responded to the stimulus and no button push means that the subject did not notice the stimulus. The input device 106 may also be a linear capacitive touch sensor or analog slider for variable input, and the variable input may determine how much the subject noticed the stimulus. For example, the variable input device may be a touch screen of a smartphone, and a subject may tap the top of the touch screen to indicate a strong stimulus, tap the bottom of the touch screen to indicate a weak stimulus, or vice versa. The input device 106 may also be biopotential electrodes or an imaging device measuring neural activity. Alternatively, the input device 106 may be a camera measuring pupil diameter. If the input device 106 measures either neural activity or pupil dilation, the main processing unit 102 may be further configured to interpret the data provided by the input device 106 to find and determine meaningful changes in neural activity or pupil dilation.

As described above, the psychometric testing system may be adapted to many different types of psychometric tests, including but not limited to, audio testing, visual testing, somatosensory testing, and the like. For illustration purposes, the detailed disclosure will frequently describe the system and methods employed herein in terms of an audiogram. Any description of an audiogram is not limiting as the system and methods may be adapted for other types of psychometric tests.

The main processing unit 102 estimates a detection threshold using machine learning that adjusts sampling across all variables according to greatest uncertainty in the current estimate of the global function. In the audiogram case, any frequency and intensity could be selected for stimulus delivery on any trial, depending solely upon the estimate uncertainly over both frequency and intensity.

The machine learning algorithm applies a Gaussian process regression algorithm to construct detection threshold estimates in real time. The Gaussian process regression allows for rapid and accurate estimation of multidimensional surfaces by constructing a Bayesian estimate of a function based upon prior distribution of probabilities for that function. The Gaussian process regression function includes a posterior function based upon a variable space, a covariance function and several hyperparameters. To assist in data collection for the Gaussian process, the main processing unit 102 executes an informative real-time sampling technique calculation technique based on Bayesian estimation. Each component of the Gaussian process regression algorithm will be discussed in further detail below.

The variable space for the Gaussian process regression algorithm depends upon the sensory organ being tested. For example, an audiogram may have the variable space of sound frequency and intensity. For visual testing, the variable space may be x and y coordinates in a visual field. The Gaussian process regression algorithm must be trained for each given variable. For example, for an audiogram, there will be intensities for a given frequency that are audible for most people; these values have a probability of detection equal to 1. In addition, there will be intensities for a given frequency that are inaudible for almost all humans; these variables have a probability of detection equal to 0. However, there are intensity values where the probability of detection is between 0 and 1 near the detection threshold. These intensity and frequency values at or around the detection threshold are tones that may be heard only occasionally or under the right circumstances, such as when the heart is between beats, or when a person is listening very closely. These probability values between 0 and 1 found by the posterior probability function are helpful in determining the function that represents the detection threshold estimate. As the main processing unit 102 performs more trials, the main processing unit 102 generates a better estimate of the detection threshold estimate across audible frequencies.

For an audiogram, the response function estimate can be written as:

$$R(I,f)$$

where I is the intensity of a pure tone and f is the frequency of the tone. R takes on values of 1 for the combination of frequencies and intensities that can be heard and values of 0 for combinations that cannot be heard. The response function contour where R takes on a particular value, typically 0.5 or 0.707, is often used to summarize the entire function. The audiogram, for example, may be represented as $$A(f)=R(I=0.5 \text{ or } 0.707,f)$$

Traditional methods, such as the Hughson-Westlake method, cannot estimate A(f) directly, and A is instead estimated at a few discrete frequency values (typically 0.25, 0.5, 1, 2, 4, 8 kHz). The methods described herein can estimate the entire function.

The covariance function describes how variables of interest change with one another. Generally, the covariance function describes the smoothness of the Gaussian process function in each dimension. The covariance function incorporates constraints that reflect prior knowledge about psychometric functions. First, these constraints and prior knowledge assume that there is only one detection threshold for any frequency. That is, the probability of detection for a tone is typically monotonically increasing as a function of intensity. However, the probability of detection for a tone need not have an explicit dependence upon frequency. The second constraint from prior knowledge is that the detection threshold boundary is continuous and therefore relatively smooth.

To reflect the two constraints, the main processing unit 102 calculates two separate covariance functions for the frequency dimension and the intensity dimension. These two kernels can be constrained separately for each independent variable, which allows the Gaussian process to provide an accurate estimate of the entire response function. The intensity dimension covariance function is a linear kernel in intensity ($K_L(x_1, x_2)=x_1^T x_2$). The linear kernel is used for the intensity variable to implement a constraint of monotonic increasing response values as a function of intensity. The frequency dimension covariance function is a flexible squared exponential kernel ($K_{SE}(x_1, x_2)=\exp(-|d|^2/(2l^2))$). The squared exponential kernel allows the response function to take a wide-variety of functions of frequency. Because the audiogram A(f) is only a function of frequency, this procedure places minimal constraints on the form of the derivative function.

In addition, the main processing unit 102 calculates three hyperparameters for the audiogram embodiment: a Gaussian noise parameter, an amplitude d for the squared exponential kernel, and a characteristic length scale l for the squared exponential kernel. The Gaussian noise parameter enables the Gaussian process function to ignore false positives and false negatives. In other embodiments, the main processing unit 102 may respond to false positives and false negatives by generating the same tone again and testing the same tone over again. Detecting and retesting false positives and false negatives improves the accuracy of the estimated function.

Further still, the main processing unit 102 calculates a predictive posterior function after each trial. The main processing unit 102 uses all the data previously gathered through samples to calculate posterior probabilities for samples that have not been evaluated. At a frequency and intensity pair, the posterior probability about the Gaussian process function is a Gaussian distribution and encodes both the posterior probability of detection at that frequency and intensity, as well as a natural measure of confidence. These posterior probability distributions can be computed with standard Gaussian process inference techniques.

The main processing unit 102 estimates the detection threshold extremely efficiently by employing a technique called informative sampling. The informative sampling technique is based upon Bayesian active learning. The main processing unit 102 efficiently samples over all variables by finding a combination of frequency and intensity that maximizes some quality measure captured in the acquisition function given the posterior. Examples include posterior variance and mutual information. The main processing unit 102 determines sampling parameters, such as frequency and intensity for audio testing, based upon the posterior, using data from the previous iteration. The main processing unit 102 calculates the acquisition function for numerous pairs of frequency and intensity. On average, tests in patients have shown that an audiogram can be estimated using no more than 39 samples. The main processing unit 102 picks the variable combination corresponding to the highest value in the acquisition function, wherein the highest value in the acquisition function represents the most informative tone. If multiple points are tied for maximum acquisition function value, the main processing unit 102 randomly selects one of the multiple tied points. Once the main processing unit 102 determines a point of maximum quality, the main processing unit 102 generates a signal commanding the stimulus inducer 104 to generate a tone having the frequency and intensity corresponding to the point of maximum quality. If the psychometric test is not audio, the main processing unit 102 may generate a signal commanding the stimulus inducer 104 to generate a stimulus corresponding to the values that maximize the acquisition function for the sensory organ under test.

Figure 2:
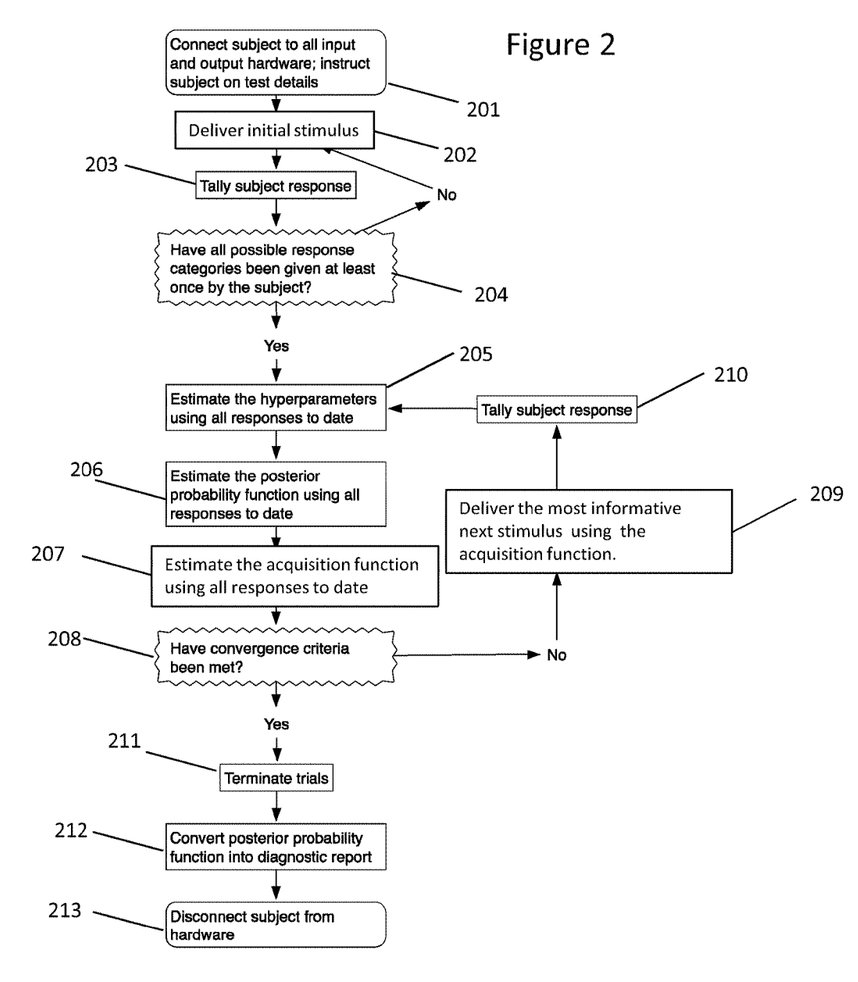
FIG. 2 illustrates a flow chart for performing the psychometric test.

Referring now to FIG. 2, a method for estimating the detection threshold is illustrated. In the description of the flowcharts, the functional explanation marked with numerals in angle brackets, <nnn>, will refer to the flowchart blocks bearing that number. First, initial set-up steps, such as setting up the stimulus delivery system, are performed. The initial set-up involves connecting the stimulus inducer 104 to the subject so that the main processing unit 102 may stimulate the subject <201>. Additionally, a psychometrician will set up the response system that allows the subject to report when he or she responded to the stimulus. This set-up step may involve giving the subject a button to press, connecting electrodes or imaging devices measuring neural activity, or attaching other devices measuring physiological variables, such as galvanic skin response or pupil dilation, to the subject.

Referring again to FIG. 2, the method continues when the main processing unit 102 commands the stimulus inducer 104 to apply a stimulus selected by the main processing unit 102 <202>. The main processing unit 102 selects the first stimulus randomly from all possible values of the independent variables. After applying the stimulus, the main processing unit 102 logs the subject's response based upon whether the main processing unit 102 received a signal from the input device 106 <203>. In an audiogram, the input device 106 may indicate whether the subject heard the tone. The main processing unit 102 determines that a person heard the tone if the main processing unit 102 receives a response through the input device 106 within a predetermined time frame of ceasing the stimulation applied by the stimulus inducer 104. For example, the predetermined time frame may be two (2) seconds.

The main processing unit 102 continues to randomly select stimulus parameters (e.g. frequency and intensity) that are different than the first stimulus, commands the stimulus inducer 104 to apply the stimulus according to the selected parameters, and logs subject response until the main processing unit 102 determines that it has received a response from all response categories. For the audiogram example, there are two response categories: a heard tone and an unheard tone. It should be noted that not all psychometric tests have two response categories. If the main processing unit 102 has not received at least one response from each response category, the main processing unit 102 continues to deliver random tones until the main processing unit 102 has logged at least one of each response category <204>. The main processing unit 102 may incorporate prior knowledge or prior test results to speed up the initial random stimulus process. For example, in the audiogram example, the main processing unit 102 may intentionally play tones that are far away from an expected detection threshold, either above or below the detection threshold, to finish the initialization process after very few stimuli. However, learning from stimuli that are not relatively near the detection threshold are not particularly interesting or informative as to the true detection threshold location. Thus, in an alternative embodiment, the main processing unit 102 may randomly select initial tones that are near an expected detection threshold location to gain maximum information during the initialization phase.

Once the main processing unit 102 has received at least one of each response category, the main processing unit then calculates an estimate of suitable hyperparameters using all the responses logged by the main processing unit <205>. In addition to calculating the hyperparameters, the main processing unit 102 calculates an estimate of the posterior probability function using all the responses logged by the main processing unit 102 <206>. In addition to calculating the posterior function, the main processing unit 102 calculates the acquisition function. The acquisition function may use all responses to date. The main processing unit 102 may also calculate the Gaussian process estimation procedure using the acquisition function <207>.

After performing these calculations, the main processing unit 102 determines whether or not the convergence criteria have been met <208>. If the convergence criteria have been met, the main processing unit 102 terminates the trial generation method <211> and converts the posterior probability function into a diagnostic report such as an audiogram curve <212>. The convergence criteria may include a particular number of stimuli, a target acquisition function value, a minimum change in posterior response function estimate as a result of the last trial, or any other convergence criteria indicating that the detection threshold estimate is sufficiently accurate. The subject can then be disconnected from the hardware <213>.

If the convergence criteria have not been met, the main processing unit 102 selects new sample parameters (e.g. frequency and intensity) using the acquisition function. The new sample parameters may be found according to the informative sampling methods described above. After selecting the new parameter, the main processing unit 102 commands the stimulus inducer 104 to apply the stimulus according to the parameters determined by the informative sampling method, and the stimulus inducer 104 applies the stimulus to the subject <209>. The main processing unit 102 logs the response to the applied stimulus and recalculates the hyperparameters, posterior probability function and acquisition function using the most recent data and all previous data. The main processing unit 102 continues to sample informatively, tally responses, and recalculate the Gaussian process unit the convergence criteria have been met <210>.

Figure 3:
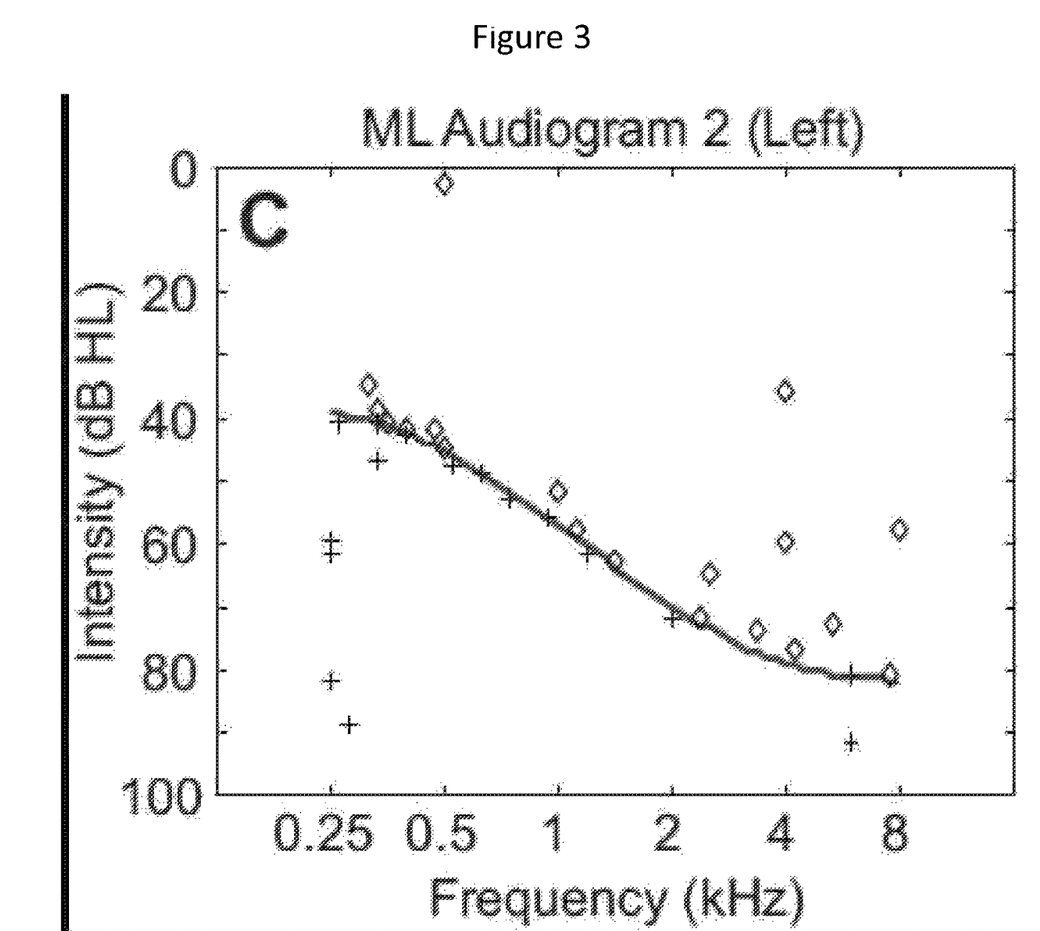
FIG. 3 illustrates an audiogram plot generated by the machine learning methods disclosed herein.

FIG. 3 illustrates a graph plotting the detection threshold for an actual subject as a result of applying the machine learning psychometric testing procedure described above. The detection threshold function plot of FIG. 3 is an audiogram detection threshold plot. The detection threshold is a continuous function of frequency from 0.25 kHz to 8 kHz. The diamond-shaped icons represent unheard tones as indicated by a subject failing to press a button on the input device 106, and the plus-shaped icons represent heard tones as indicated by a subject pressing a button on the input device 106.

As can be seen from FIG. 3, most of the diamond-shaped icons and the plus-shaped icons appear very near the final detection threshold plot. Informative sampling techniques focus upon frequency and intensity values near the detection threshold because these intensity and frequency positions have the most uncertainty, and thereby have the highest acquisition function values. The icons illustrated far away from the detection threshold plot are stimuli presented during the initial stages of data gathering when the main processing unit 102 chooses stimulus parameters at random.

Figure 4:
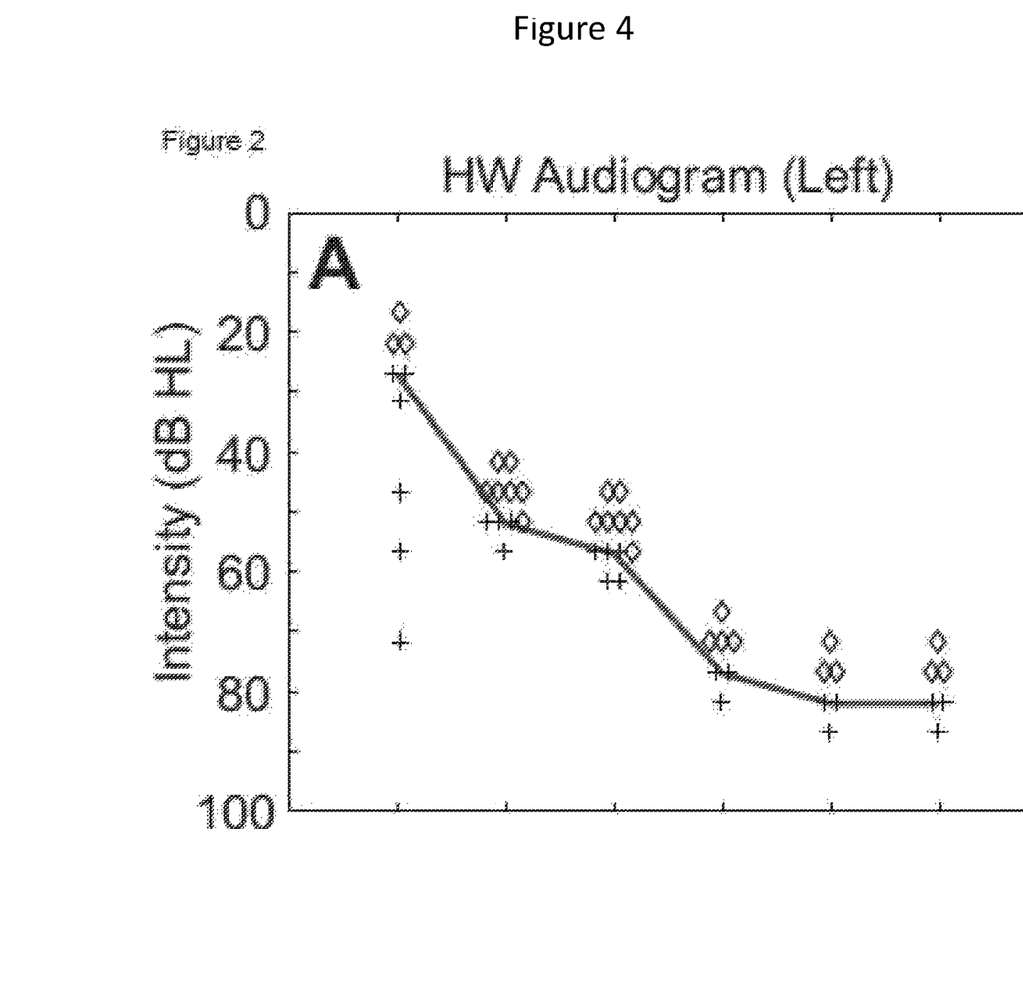
FIG. 4 illustrates an audiogram plot generated according to conventional testing techniques.

Lastly, the stimulus parameters are not constrained to the standard frequency values. The flexible stimulus points stand in stark contrast to a normal audiogram plot, such as the conventional audiogram plot shown in FIG. 4, which illustrates the conventional methods for audiogram data acquisition. As shown in FIG. 4, data are collected only at the six standard frequencies. Thus, because the psychometric testing procedure described herein gathers data across all audible frequencies, the detection threshold estimate is more accurate at all frequencies, and especially more accurate at the nonstandard frequencies.

Figure 5:
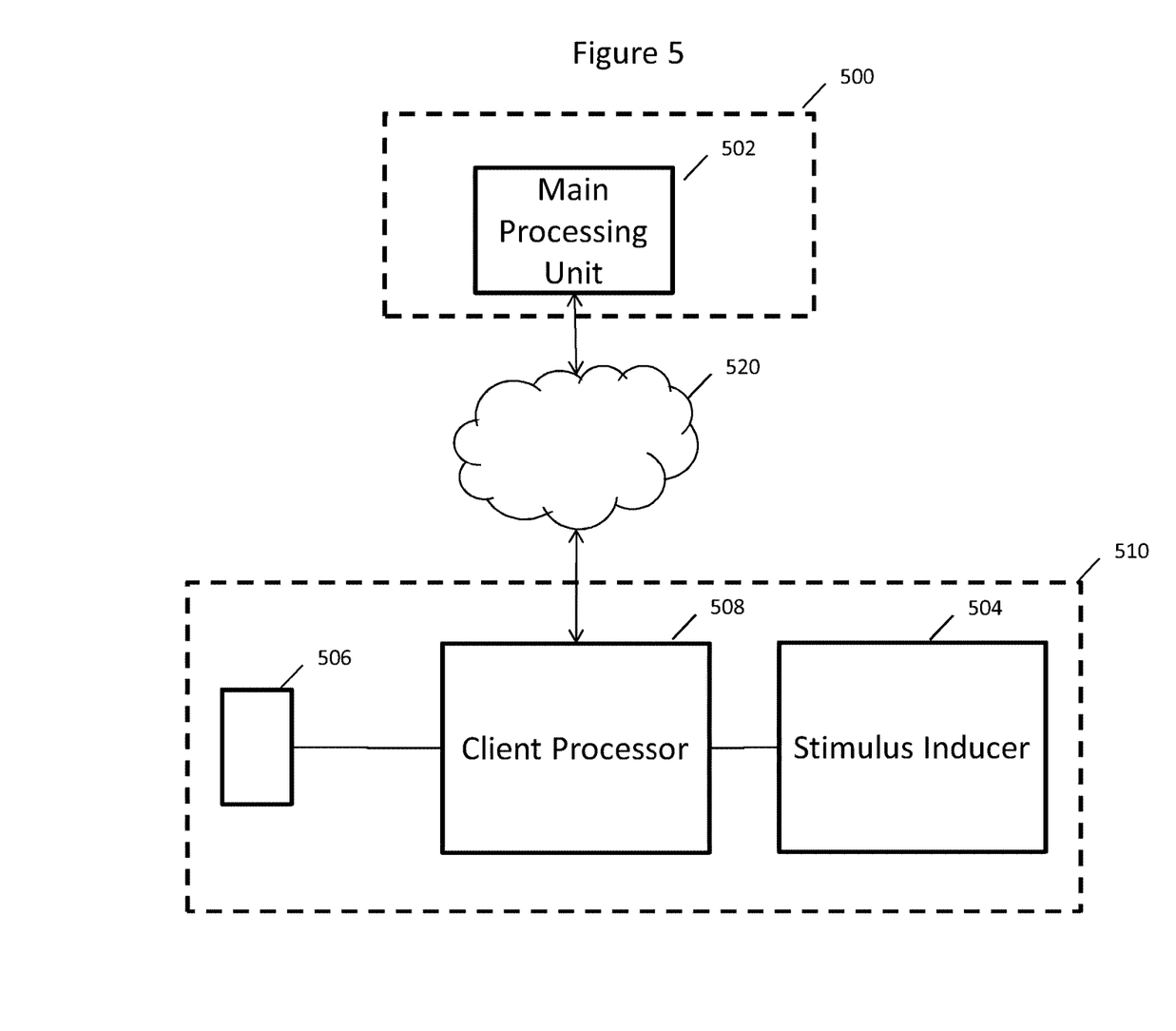
FIG. 5 illustrates a network-based system used to administer the psychometric test according to an exemplary embodiment.

FIG. 5 illustrates an alternative embodiment to the system of FIG. 1 where the input device and the stimulus inducer are remotely located. FIG. 5 illustrates two distinct computer systems: a host computer system 500 and a client computer system 510. The host computer system 500 and the client computer system 510 communicate through a network 520. The network 520 may be a wide area network or a local area network. Furthermore, the network 520 may be a wired, wireless, cellular, or any other type of network.

The host computer system 500 includes the main processing unit 502 that is configured similarly to the main processing unit 102 of FIG. 1. However, the main processing unit 502 is further configured to communicate over the network 520 and send commands to the stimulus inducer 504 and the input device 506 through network protocol. The main processing unit 502 may be configured to communicate with numerous client computer systems 510. For example, the host computer system may be configured as a cloud server. In this way, the host computer system may perform psychometric tests over the Internet.

The client computer system 510 includes a client processor 508. The client processor 508 communicates with the main processing unit 502 through the network 520 using network protocol. The client processor 508 receives the commands from the main processing unit 502, and the client processor 508 commands the stimulus inducer 504 to stimulate a subject in response to the commands received from the main processing unit 502 and according to the parameters set by the main processing unit 502. The client processor 508 also receives responses through the input device 506, and the client processor 508 reports any subject responses made through the input device 506 to the main processing unit 502 over the network 520.

The stimulus inducer 504 may be configured similarly to the stimulus inducer 104 of FIG. 1. Furthermore, the stimulus inducer 504 may comprise any of the devices described above with reference to FIG. 1. The input device 506 may be configured similarly to the input device 106 of FIG. 1. The input device 506 may also comprise a device already connected to the client processor 508, such as a mouse or keyboard.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method of machine learning psychometric testing of sensory information comprising:
   randomly selecting, via a processor, stimulus parameters for a first stimulus to be applied with a stimulus inducer;
   applying the first stimulus on a subject with the stimulus inducer upon command of the processor;
   calculating (i) a plurality of hyperparameters, (ii) a posterior probability function, and (iii) an acquisition function, at least based on the subject's response to the first stimulus with the processor;
   determining stimulus parameters for a second stimulus based on the calculated acquisition function with the processor;
   stimulating the subject with the second stimulus with the stimulus inducer upon command of the processor;
   recalculating (i) the plurality of hyperparameters, (ii) the posterior probability function, and (iii) the acquisition function, at least based on the subject's response to the second stimulus with the processor;
   determining, by informative sampling, a detection threshold function by calculating the posterior probability function at least based on the subject's response to the second stimulus with the processor; and
   operating, by the subject, an input device, wherein the processor receives subject responses based on data received from the input device and the input device sends signals to the processor indicating whether the subject responded to the first stimulus or the second stimulus.

2. The method of machine learning psychometric testing of sensory information of claim 1, wherein the stimulus inducer is a loudspeaker or headphones and the first stimulus is a tone having a frequency and an intensity and the second stimulus is a tone having a frequency and an intensity.

3. The method of machine learning psychometric testing of sensory information of claim 1, wherein the stimulus inducer is a light field or a visual display, and the first stimulus is light or visual stimulus having (x, y) coordinates in the light field or the visual display and the second stimulus is light or visual stimulus having (x, y) coordinates in the light field or the visual display.

4. The method of machine learning psychometric testing of sensory information of claim 1, wherein the stimulus inducer is a refreshable braille display, and the first stimulus is pressure on the subject's skin having a location and a force and the second stimulus is pressure on the subject's skin having a location and a force.

5. The method of machine learning psychometric testing of sensory information of claim 1, wherein the input device is a binary input button.

6. The method of machine learning psychometric testing of sensory information of claim 5, wherein the input device further comprises a camera that measures eye pupil dilation and the processor is further configured to convert data measuring the eye pupil dilation and determine based on the data measuring the eye pupil dilation whether the subject responded to at least one of the first stimulus and the second stimulus.

7. The method of machine learning psychometric testing of sensory information of claim 1, wherein the input device is a touch screen, wherein the subject tapping a first area of the touch screen indicates a strong stimulus and the subject the subject tapping a second area of the touch screen indicates a weak stimulus.

8. The method of machine learning psychometric testing of sensory information of claim 1, wherein the processor determines the detection threshold function by calculating the posterior probability function based on the subject's response to at least the second stimulus and the first stimulus.

9. The method of machine learning psychometric testing of sensory information of claim 1, wherein the informative sampling comprises active learning.

10. The method of machine learning psychometric testing of sensory information of claim 1, wherein the determining of the detection threshold function further comprises applying a Gaussian process regression algorithm to construct detection threshold estimates in real time.

11. The method of machine learning psychometric testing of sensory information of claim 1, wherein the plurality of hyperparameters comprises (i) a Gaussian noise parameter, (ii) an amplitude for a squared exponential kernel, and (iii) a characteristic length scale for the squared exponential kernel.

12. A machine learning psychometric testing system of sensory information comprising:
a stimulus inducer configured to apply a stimulus to a subject;
an input device configured to send data indicating whether the subject responded to the stimulus applied by the stimulus inducer; and
a processor configured to randomly select stimulus parameters for a first stimulus to be applied to a subject, command the stimulus inducer to stimulate the subject with the first stimulus, receive data from the input device indicating whether the subject responded to the first stimulus, calculate (i) a plurality of hyperparameters, (ii) a posterior probability function, and (iii) an acquisition function, at least based on the subject's response to the first stimulus, determine stimulus parameters for a second stimulus based on the calculated acquisition function, command the stimulus inducer to stimulate the subject with the second stimulus, recalculate (i) the plurality of hyperparameters, (ii) the posterior probability function, and (iii) the acquisition function, at least based on the subject's response to the second stimulus, receive a signal from the input device indicating whether the subject responded to the second stimulus, and determine, by informative sampling, a detection threshold function by calculating the posterior probability function based on the subject's response to at least the second stimulus.

13. The machine learning psychometric testing system of sensory information of claim 12, wherein the stimulus inducer is a loudspeaker or headphones and the first stimulus is a tone having a frequency and intensity and the second stimulus is a tone having a frequency and intensity.

14. The machine learning psychometric testing system of sensory information of claim 12, wherein the stimulus inducer is a light field or visual display, and the first stimulus is light or visual stimulus having (x, y) coordinates in the light field or visual display and the second stimulus is light or visual stimulus having (x, y) coordinates in the light field or visual display.

15. The machine learning system computerized psychometric testing of sensory information of claim 12, wherein the stimulus inducer is a refreshable braille display, and the first stimulus is pressure on the subject's skin having a location and a force and the second stimulus is pressure on the subject's skin having a location and a force.

16. The machine learning psychometric testing system of sensory information of claim 12, wherein the input device is a binary input button.

17. The machine learning psychometric testing system of sensory information of claim 12, wherein the input device is a touch screen, wherein the subject tapping a first area of the touch screen indicates a strong stimulus and the subject the subject tapping a second area of the touch screen indicates a weak stimulus.

18. The machine learning psychometric testing system of sensory information of claim 12, wherein the processor determines the detection threshold function by calculating the posterior probability function based on the subject's response to at least the second stimulus and the first stimulus.

19. A method for informative machine learning psychometric test sampling comprising:
calculating (i) a plurality of hyperparameters, and (ii) an acquisition function of a predictive posterior probability function;
determining, by informative sampling, a variable set contributing to a value of the acquisition function; and
stimulating a subject with a stimulus having randomly selected parameters corresponding to the variable set contributing to a highest acquisition function,
wherein the predictive posterior probability function comprises variance or mutual information.

* * * * *